US010702624B2

(12) United States Patent
Peterson (10) Patent No.: US 10,702,624 B2
(45) Date of Patent: Jul. 7, 2020

(54) AIR DUCT STERILIZATION SYSTEM AND DEVICE AND METHOD FOR PRODUCTION

(71) Applicant: James Peterson, Archer, FL (US)

(72) Inventor: James Peterson, Archer, FL (US)

( * ) Notice: Subject to any disclaimer, the term of this patent is extended or adjusted under 35 U.S.C. 154(b) by 0 days.

(21) Appl. No.: 16/124,308

(22) Filed: Sep. 7, 2018

(65) Prior Publication Data

US 2019/0076569 A1 Mar. 14, 2019

Related U.S. Application Data

(60) Provisional application No. 62/556,259, filed on Sep. 8, 2017.

(51) Int. Cl.
| | |
|---|---|
| *A61L 9/20* | (2006.01) |
| *B08B 7/00* | (2006.01) |
| *B08B 9/027* | (2006.01) |
| *F16L 55/24* | (2006.01) |
| *A61L 2/10* | (2006.01) |
| *F16L 55/28* | (2006.01) |
| *B23P 19/04* | (2006.01) |
| *F16L 101/18* | (2006.01) |
| *F16L 9/00* | (2006.01) |

(52) U.S. Cl.
CPC ............ *A61L 9/20* (2013.01); *A61L 2/10* (2013.01); *B08B 7/0057* (2013.01); *B08B 9/027* (2013.01); *F16L 55/24* (2013.01); *F16L 55/28* (2013.01); *A61L 2202/11* (2013.01); *A61L 2202/16* (2013.01); *A61L 2209/12* (2013.01); *A61L 2209/15* (2013.01); *A61L 2209/16* (2013.01); *B23P 19/04* (2013.01); *F16L 9/003* (2013.01); *F16L 2101/18* (2013.01)

(58) Field of Classification Search
USPC ....................................................... 250/435
See application file for complete search history.

(56) References Cited

U.S. PATENT DOCUMENTS

| | | | | |
|---|---|---|---|---|
| 5,558,158 | A | * | 9/1996 | Elmore ..................... A61L 9/20 165/122 |
| 6,589,476 | B1 | | 7/2003 | Fencl |
| 6,627,000 | B2 | | 9/2003 | Fencl et al. |
| 8,038,949 | B2 | | 10/2011 | Horne et al. |
| 8,242,518 | B2 | * | 8/2012 | Lerman ............... H01L 25/0753 257/88 |

(Continued)

*Primary Examiner* — Phillip A Johnston
(74) *Attorney, Agent, or Firm* — Boudwin Intellectual Property; Daniel Boudwin (57) ABSTRACT

An air duct sterilization system, and a device and method for producing the air duct sterilization system. The system includes a plurality of ultraviolet light-emitting diodes (UV LEDs), arranged in a UV LED strip within an air duct, configured to destroy airborne biological contaminants in the air duct. The device includes wheel assemblies and an applicator assembly. During installation of the UV LED strip, the wheel assemblies contact a lower surface and an upper surface of an interior of the air duct, thereby enabling the device to roll along the interior of the air duct. The UV LED strip is applied to the upper surface of the interior of the air duct using the applicator assembly, with minimal effort needed from an individual performing the installation. After installation, the UV LEDs are illuminated as needed to destroy airborne biological contaminants, thereby sterilizing the air duct and air therein.

15 Claims, 7 Drawing Sheets

(56) References Cited

U.S. PATENT DOCUMENTS

| | | | |
|---|---|---|---|
| 8,421,689 B2* | 4/2013 | Schlub | H01Q 1/243 343/700 MS |
| 9,974,881 B2* | 5/2018 | Kim | A61L 2/00 |
| 10,039,852 B2* | 8/2018 | Yi | F24F 1/0071 |
| 2002/0104972 A1 | 8/2002 | Guzorek | |
| 2008/0194009 A1 | 8/2008 | Marentis | |

* cited by examiner

AIR DUCT STERILIZATION SYSTEM AND DEVICE AND METHOD FOR PRODUCTION

CROSS REFERENCE TO RELATED APPLICATIONS

This application claims priority under 35 U.S.C. § 119(e) to U.S. Provisional Application No. 62/556,259 filed on Sep. 8, 2017. The above identified patent application is incorporated by reference herein in its entirety to provide continuity of disclosure.

BACKGROUND OF THE INVENTION

The present invention relates to an air duct sterilization system for sterilizing an air duct, and a device and method for producing the system.

Contamination of air ducts by biological contaminants, including mold, bacteria, and viruses, is a growing threat to a safety of public and private structures having air ducts. These biological contaminants are often airborne, and efforts to contain and neutralize them are critical for effectively combating a spread of a disease or a biological weapon. These efforts include regularly cleaning an air duct, and filtering an air inside the air duct. Cleaning the air duct is labor and cost-intensive, and filtering the air inside the air duct with an air filter increases a load on a forced air system pumping the air through the air duct, thereby decreasing energy efficiency and increasing cost.

Irradiating the air duct and the air therein with radiation, such as ultraviolet (UV) radiation, is an effective approach to neutralize these contaminants. UV radiation ionizes and damages nucleic acids required for the contaminants to survive, reproduce, and maintain pathogenicity, thereby effectively neutralizing the contaminants with minimal intervention. However, traditional sources of UV radiation, such as mercury arc lamps, are often unsafe, require frequent maintenance and replacement, and are energy inefficient. UV light-emitting diodes (UV LEDs), a relatively new source of UV radiation, are safe, require minimal maintenance and replacement, and are energy efficient, making them an important improvement in UV technology. In addition, compared to disposal of mercury arc lamps, disposal of UV LEDs is environmentally friendly and cost-effective. A promising approach for an air duct sterilization system uld include using UV LEDs in the air duct. However, installing UV LEDs into new air ducts, as well as existing air ducts, is labor-intensive and cost-inefficient.

Therefore, there is a need in the art for an air duct sterilization system, and a device and method for conveniently and efficiently producing the air duct sterilization system. The present invention addresses this unmet need.

Devices have been disclosed in the art that relate to air duct sterilization systems. These include systems that have been patented and published in patent application publications. These devices are often labor-intensive and cost-inefficient. In view of the systems disclosed in the art, it is submitted that there is a need in the art for an improvement to existing air duct sterilization systems. In view of the present disclosure, it is submitted that the present invention substantially diverges in structural and functional elements from devices in the art, and substantially fulfills an unmet need in the art.

SUMMARY OF THE INVENTION

In view of the disadvantages inherent in the known types of air duct sterilization systems in the art, the present invention provides a new and improved air duct sterilization system, wherein the same can be utilized for neutralizing biological contaminants within an air duct.

In one aspect, the invention provides a device for installing a plurality of ultraviolet light-emitting diodes (UV LEDs) in an air duct. The device includes a central axle, a left wheel assembly, a right wheel assembly, and an applicator assembly. The left wheel assembly and the right wheel assembly are disposed on a left end and a right end of the central axle, respectively, and include a plurality of guide wheels disposed thereon configured to guide the device through the air duct during installation of the plurality of UV LEDs. The applicator assembly is disposed on an intermediate portion of the central axle between the left end and the right end, and includes a plurality of applicator rolls configured to exert an upward force to press the plurality of UV LEDs against an upper surface of an interior of the air duct during installation of the plurality of UV LEDs.

In another aspect, the invention provides a method for installing a plurality of UV LEDs in an air duct, comprising exerting an upward force to press the plurality of UV LEDs against an upper surface of an interior of the air duct, and guiding the upward force along the interior of the air duct. In particular embodiments, the method utilizes the device.

In another aspect, the invention provides an air duct sterilization system, comprising an air duct, and a plurality of UV LEDs secured to an upper surface of an interior of the air duct. In particular embodiments, the air duct sterilization system is produced by the method. In preferred embodiments, the air duct sterilization system is produced by the method that utilizes the device.

It is therefore an object of the present invention to provide an air duct sterilization system for neutralizing biological contaminants within an air duct.

Another object of the present invention is to provide an installation device, and a method of using the installation device to produce the air duct sterilization system.

Another object of the present invention is to provide an air duct sterilization system and installation device that may be readily manufactured from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of the invention will be particularly pointed out in the claims, the invention itself and manners in which it may be made and used may be better understood after a review of the following description, taken in connection with the accompanying drawings, wherein like numeral annotations are provided throughout.

DETAILED DESCRIPTION OF THE INVENTION

Reference is made herein to the attached drawings. Like reference numerals are used throughout the drawings to depict like or similar elements of the portable air filtration device and method. The figures are intended for representative purposes only and should not be considered limiting in any respect.

Figure 1:
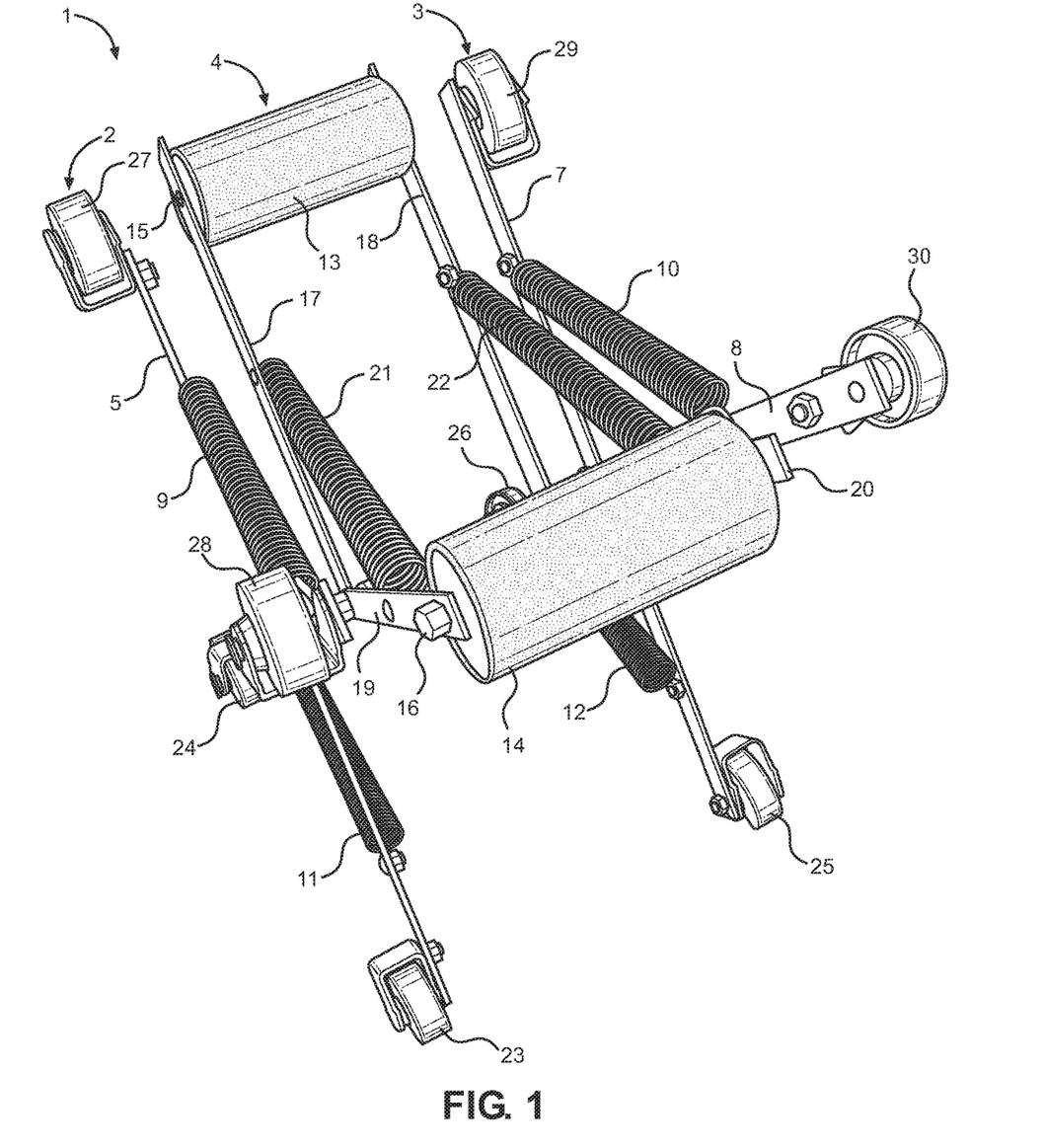
FIG. 1 depicts a perspective view of an exemplary installation device.
Figure 2:
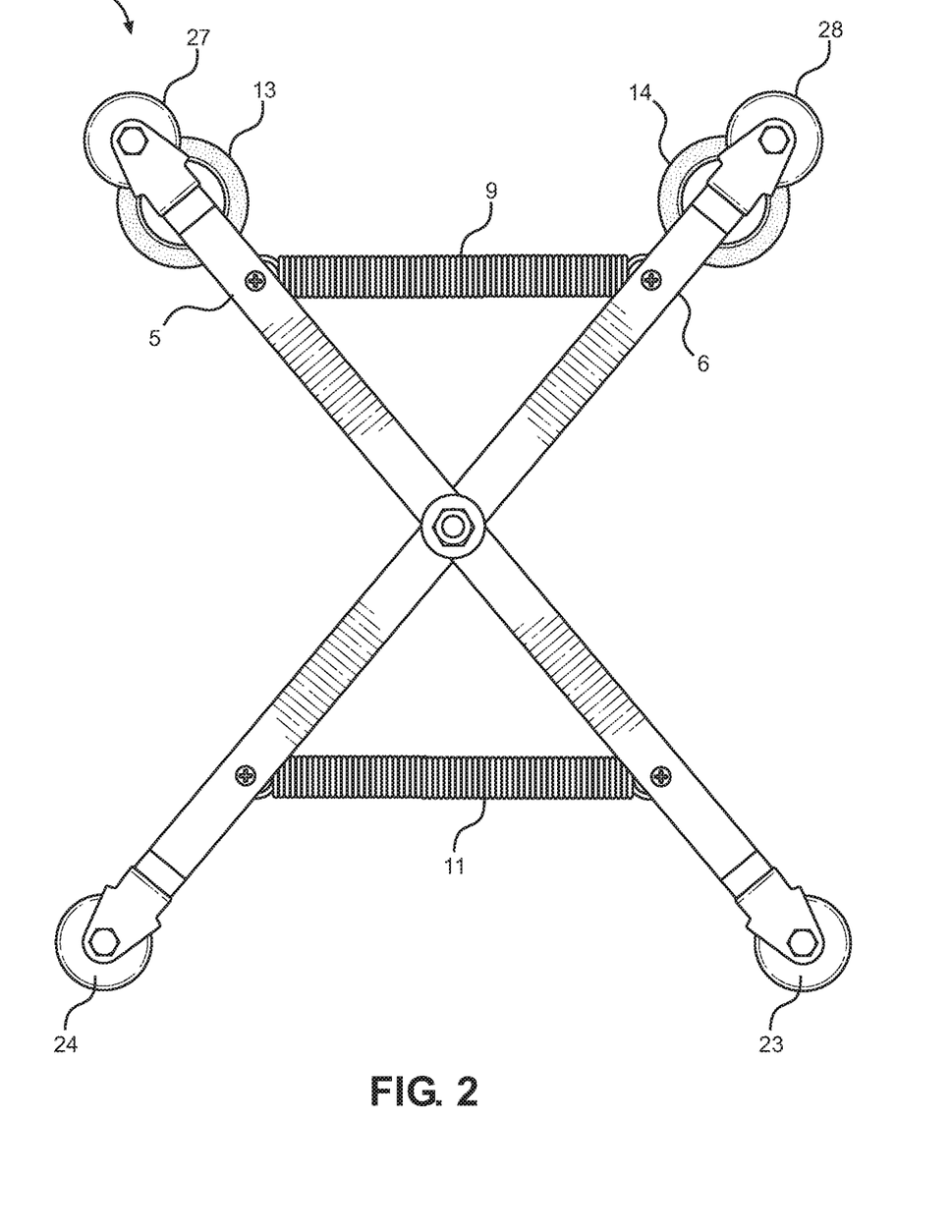
FIG. 2 depicts a side view of the exemplary installation device.

Referring now to FIGS. 1 and 2, there are depicted a perspective view (FIG. 1) and a side view (FIG. 2) of an exemplary installation device. An installation device 1, for installing a plurality of ultraviolet light-emitting diodes (UV LEDs) in an air duct, includes a central axle, a left wheel assembly 2, a right wheel assembly 3, and an applicator assembly 4. The left wheel assembly 2 is disposed on a left end of the central axle, and includes a plurality of left guide wheels disposed thereon configured to guide the installation device 1 through the air duct during installation of the plurality of UV LEDs. The right wheel assembly 3 is disposed on a right end of the central axle, and includes a plurality of right guide wheels disposed thereon configured to guide the installation device 1 through the air duct during installation of the plurality of UV LEDs. The applicator assembly 4 is disposed on an intermediate portion of the central axle between the left end and the right end thereof, and includes a plurality of applicator rolls configured to exert an upward force to press the plurality of UV LEDs against an upper surface of an interior of the air duct during installation of the plurality of UV LEDs. In this manner, an individual installing the plurality of UV LEDs into the air duct does not need to crawl through the air duct, thereby reducing a labor and a cost of installing the UV LEDs, as described elsewhere herein.

In some embodiments, the left wheel assembly 2 includes a first guide leg 5 pivotally disposed on the left end of the central axle, and a second guide leg 6 pivotally disposed on the left end of the central axle, and the right wheel assembly 3 includes a third guide leg 7 pivotally disposed on the right end of the central axle, and a fourth guide leg 8 pivotally disposed on the right end of the central axle. In some embodiments, the first guide leg 5 and the second guide leg 6 are connected in a scissor configuration and are biased by a biasing mechanism configured to apply an upward stabilizing force to the upper surface of the interior of the air duct during installation of the plurality of UV LEDs, and the third guide leg 7 and the fourth guide leg 8 are connected in a scissor configuration and are biased by a biasing mechanism configured to apply the upward stabilizing force to the upper surface of the interior of the air duct during installation of the plurality of UV LEDs. In this manner, construction of the installation device 1 is simplified, and the biasing mechanism may include any means according to necessity or availability of materials.

In some embodiments, the biasing mechanism of the first guide leg 5 and the second guide leg 6 includes a left upper spring 9 attached on a forward end thereof to an upper portion of the first guide leg 5, and attached on a rearward end thereof to an upper portion of the second guide leg 6. In some embodiments, the biasing mechanism of the third guide leg 7 and the fourth guide leg 8 includes a right upper spring 10 attached on a forward end thereof to an upper portion of the third guide leg 7, and attached on a rearward end thereof to an upper portion of the fourth guide leg 8. In this manner, a minimal number of springs is provided so as to generate the upward stabilizing force during installation of the UV LEDs, thereby reducing an amount of material needed to construct the installation device 1.

In some embodiments, the biasing mechanism of the first guide leg 5 and the second guide leg 6 includes a left lower spring 11 attached on a forward end thereof to a lower portion of the first guide leg 5, and attached on a rearward end thereof to a lower portion of the second guide leg 6. In some embodiments, the biasing mechanism of the third guide leg 7 and the fourth guide leg 8 includes a right lower spring 12 attached on a forward end thereof to a lower portion of the third guide leg 7, and attached on a rearward end thereof to a lower portion of the fourth guide leg 8. In this manner, an increased number of springs is provided so as to stabilize or maximize the upward stabilizing force during installation of the UV LEDs, thereby, prolonging a lifetime of the springs, or increasing a magnitude of the upward stabilizing force so applied.

In some embodiments, the plurality of applicator rolls 4 includes a forward applicator roll 13 and a rearward applicator roll 14. The forward applicator roll 13 is rotatably attached to a forward applicator axle 15, and the rearward applicator roll 14 is rotatably attached to a rearward applicator axle 16. A left forward applicator arm 17 is rotatably attached to a left end of the forward applicator axle 15 and pivotally attached to the intermediate portion of the central axle, and a right forward applicator arm 18 is rotatably attached to a right end of the forward applicator axle 15 and pivotally attached to the intermediate portion of the central axle. A left rearward applicator arm 19 is rotatably attached to a left end of the rearward applicator axle 16 and pivotally attached to the intermediate portion of the central axle, acrd a right rearward applicator arm 20 is rotatably attached to a right end of the rearward applicator axle 16 and pivotally attached to the intermediate portion of the central axle. In this manner, the installation device 1 is sized or proportioned so as to configure the plurality of applicator rolls 4 to steadily exert the upward force in a continuous rolling motion along the interior of the air duct during installation of the plurality of UV LEDs.

In some embodiments, the left forward applicator arm 17 and the left rearward applicator arm 19 are connected in a scissor configuration and are biased by a biasing mechanism configured to exert the upward force to the upper surface of the interior of the air duct during installation of the plurality of UV LEDs. In some embodiments, the right forward applicator arm 18 and the right rearward applicator arm 20 are connected in a scissor configuration and are biased by a biasing mechanism configured to exert the upward force to the upper surface of the interior of the air duct during installation of the plurality of UV LEDs. In this manner, a size or a proportion of the installation device 1 may not exactly fit to a single size or proportion of air duct, but enables a range of differently-sized air ducts to accept the installation device 1 therethrough for installation of the plurality of UV LEDs. In this manner, a utility of the installation device 1 is maximized.

In some embodiments, the biasing mechanism of the left forward applicator arm 17 and the left rearward applicator arm 19 includes a left applicator spring 21 attached on a forward end thereof to an upper portion of the left forward applicator arm 17, and attached on a rearward end thereof to an upper portion of the left rearward applicator arm 19. In some embodiments, the biasing mechanism of the right forward applicator arm 18 and the right rearward applicator arm 20 includes a right applicator spring 22 attached on a forward end thereof to an upper portion of the right forward applicator arm 18, and attached on a rearward end thereof to an upper portion of the right rearward applicator arm 20. In this manner, an effective number of springs is provided so as to exert the upward force during installation of the UV LEDs, thereby minimizing an amount of material needed to construct the installation device 1.

In some embodiments, the plurality of left guide wheels includes a left lower rearward wheel 23 disposed on a lower end of the first guide leg 5, and a left lower forward wheel 24 disposed on a lower end of the second guide leg 6, and the plurality of right guide wheels includes a right lower rearward wheel 25 disposed on a lower end of the third guide leg 7, and a right lower forward wheel 26 disposed on a lower end of the fourth guide leg 8. The left lower forward wheel 24, the left lower rearward wheel 23, the right lower forward wheel 26, and the right lower rearward wheel 25 are configured to contact a lower surface of the interior of the air duct during installation of the plurality of UV LEDs. In this manner, the installation device 1 can roll along the interior of the air duct while pressing the plurality of UV LEDs against the upper surface of the interior of the air duct during installation of the plurality of UV LEDs, and the individual performing the installation does not need to crawl through the air duct or manually press upward against the upper surface to install the plurality of UV LEDs, as described elsewhere herein.

In some embodiments, the plurality of left guide wheels includes a left upper forward wheel 27 disposed on an upper end of the first guide leg 5, and a left upper rearward wheel 28 disposed on an upper end of the second guide leg 6, and the plurality of right guide wheels includes a right upper forward wheel 29 disposed on an upper end of the third guide leg 7, and a right upper rearward wheel 30 disposed on an upper end of the fourth guide leg 8. The left upper forward wheel 27, the left upper rearward wheel 24, the tight upper forward wheel 29, and the right upper rearward wheel 30 are configured to contact the upper surface of the interior of the air duct during installation of the plurality of UV LEDs. In this manner, the stability of the installation device 1 is maximized.

Figure 3:
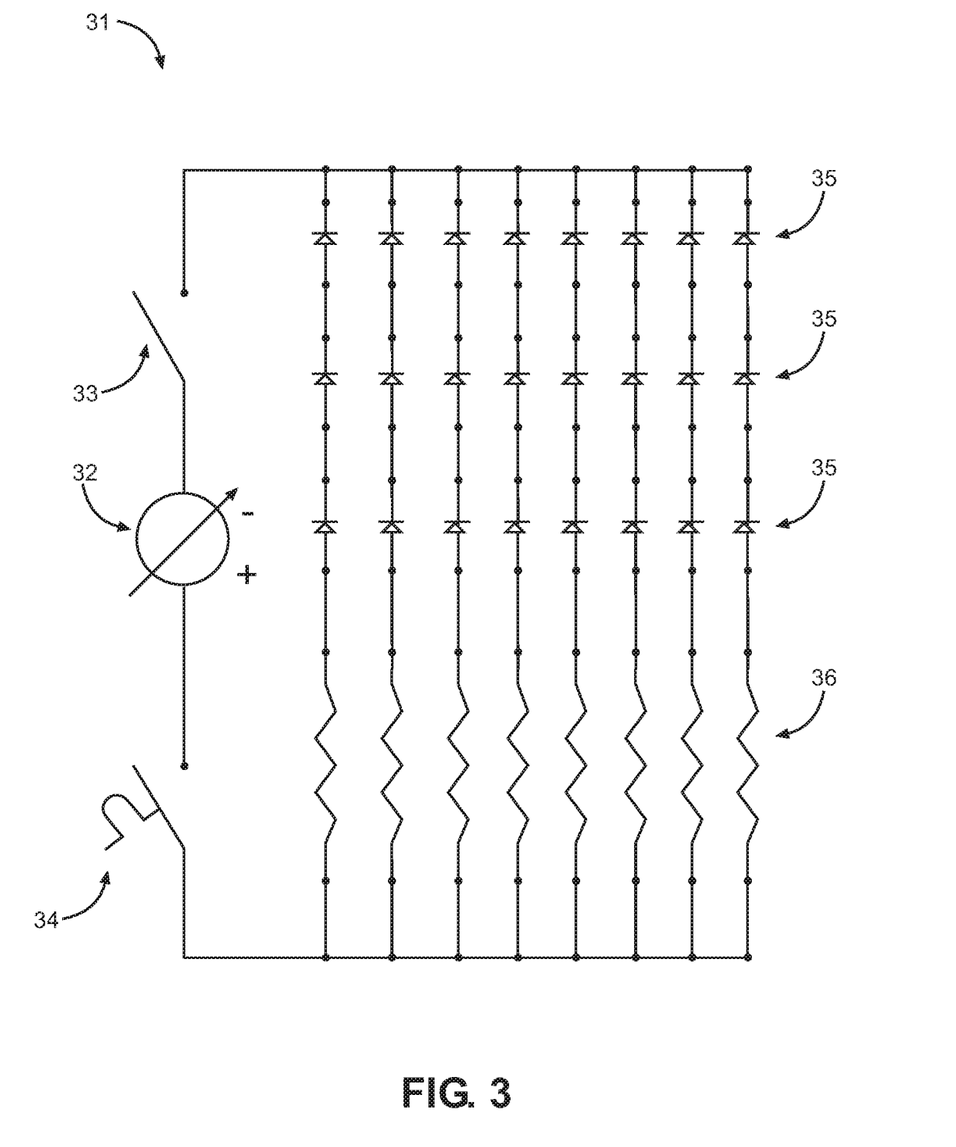
FIG. 3 depicts a circuit diagram of an exemplary UV LED circuit.

Referring now to FIG. 3, there is depicted a circuit diagram of an exemplary UV LED circuit. A UV LED circuit 31 includes a power supply 32, a switch 33, a circuit breaker 34, a plurality of UV LEDs 35, and a plurality of current-limiting resistors 36. The UV LED circuit 31 includes eight triads, each triad having three UV LEDs 35 and a current-limiting resistor 36. The current-limiting resistor 36 protects the plurality of UV LEDs 35 by limiting a magnitude of a current delivered by the power supply 32.

Figure 4:
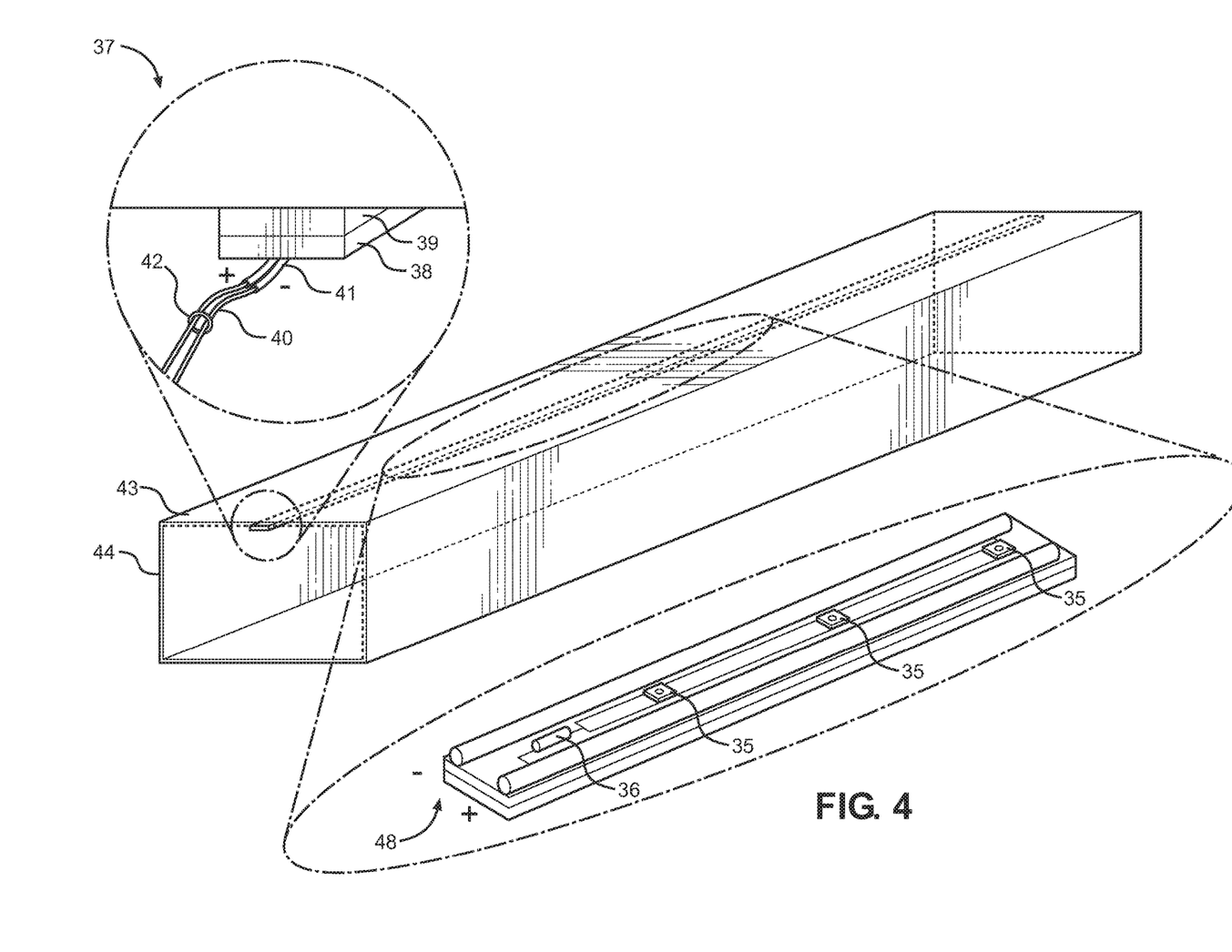
FIG. 4 depicts a perspective view of an exemplary air duct sterilization system.

Referring now to FIG. 4, there is depicted a perspective view of an exemplary air duct sterilization system. A zoomed inset of an electrical connection of the UV LED strip (left) and a zoomed inset of the UV LED strip, upside down relative to the rest of the figure (right) are depicted. In the shown embodiment, a metallic air duct 43, having a metallic air duct opening 44, includes a UV LED strip 48 installed therein. The UV LEI) strip 48 includes a strip of copper foil tape 38, having conductive adhesive thereon, configured to facilitate parallel power supply to multiple triads of UV LEDs in series. The strip of copper foil tape 38 includes a positive and a negative connection, via a low voltage wire 40, to a power supply. In the shown embodiment, the low voltage wire 40 includes a grommet 42 and a heat shrink tubing 41, which protect the low voltage wire 40 from damage during installation, use, or maintenance. A portion of the UV LED strip 48 includes the current-limiting resistor 36, and three UV LEDs 35. In particular embodiments, twenty four diodes (eight triads) are installed per sixteen feet of the metallic air duct 43, in order to sufficiently cover the interior of the metallic air duct 43 with UV radiation during use of an air duct sterilization system 37. The copper foil tape 38 is adhered to a strip of magnetic tape 39, which in turn is adhered to an upper surface of an interior of the metallic air duct 43 by ferromagnetism. In this manner, installation of the UV LED strip 48 is facilitated by a magnetic interaction between the magnetic tape 39 and the upper surface of the interior of the metallic air duct 43.

Figure 5:
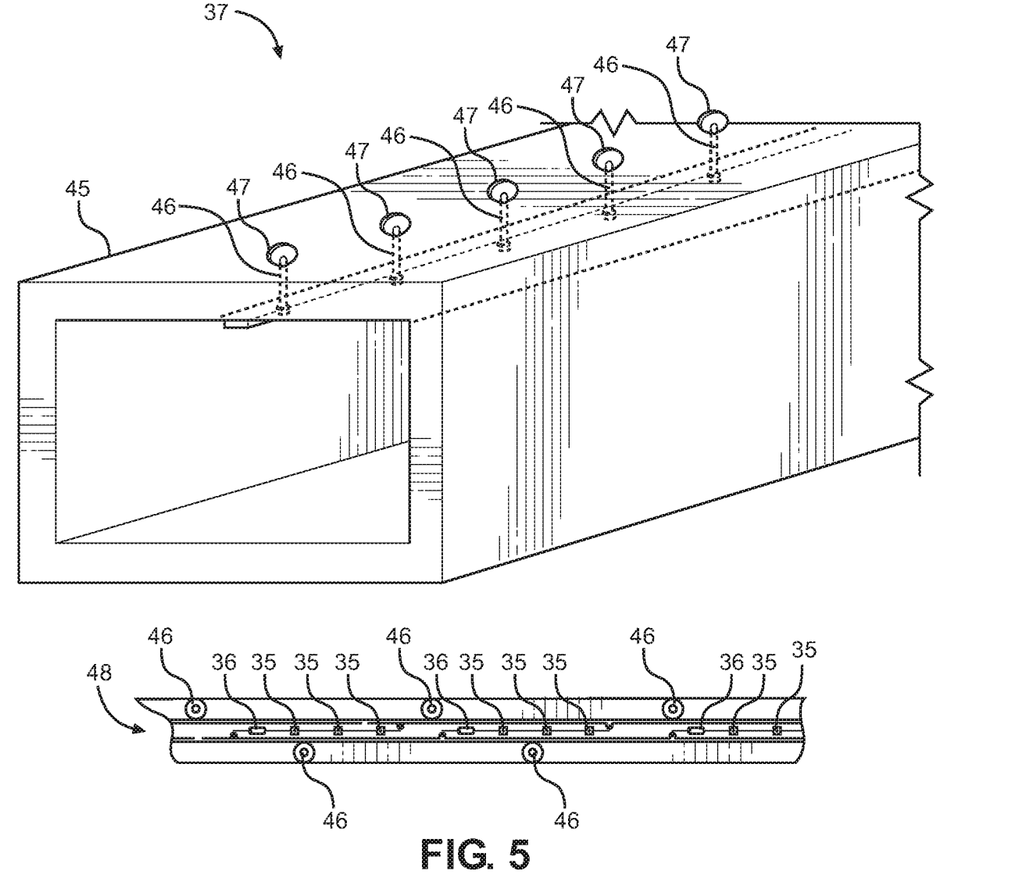
FIG. 5 depicts a perspective view of the exemplary air duct sterilization system.

Referring now to FIG. 5, there is depicted a perspective view of the exemplary air duct sterilization system. The figure includes a bottom zoomed view of the UV LEI) strip after installation (bottom). The air duct sterilization system 37 includes a ductboard air duct 45, having a plurality of anchor holes 46 drilled through an upper surface thereof, each anchor hole 46 including a cured expanded adhesive 47 which includes an upper anchor and a lower anchor, such that the upper anchor extends upward through the anchor hole 46, and the lower anchor extends downward through the anchor hole 46. The plurality of anchor holes 46 are aligned to holes drilled in a UV LED strip 48, such that each anchor hole 46 is essentially a vertical channel extending through the upper surface of the ductboard air duct 45 and through the UV LED strip 48. Unlike the metallic air duct, the ductboard air duct 45 does not contain metal, and is not able to secure the UV LED strip 48 by ferromagnetism. Therefore, anchor holes 46 are drilled through the ductboard air duct 45 and the UV LED strip 48, and the plurality of anchor holes 46 are aligned. After aligning the plurality of anchor holes 46 and pressing the UV LED strip 48 upward against the interior of the ductboard air duct 45, an expanding adhesive, such as an insulating foam sealant, is applied to fill each of the plurality of anchor holes 46. As the expanding adhesive cures, it expands, and creates the upper anchor and the lower anchor. In this manner, the UV LED strip 48 can be installed or retrofitted into any new or existing air duct, whether it is metallic (see FIG. 4) or fiberglass or ductboard (see FIG. 5).

Figure 6:
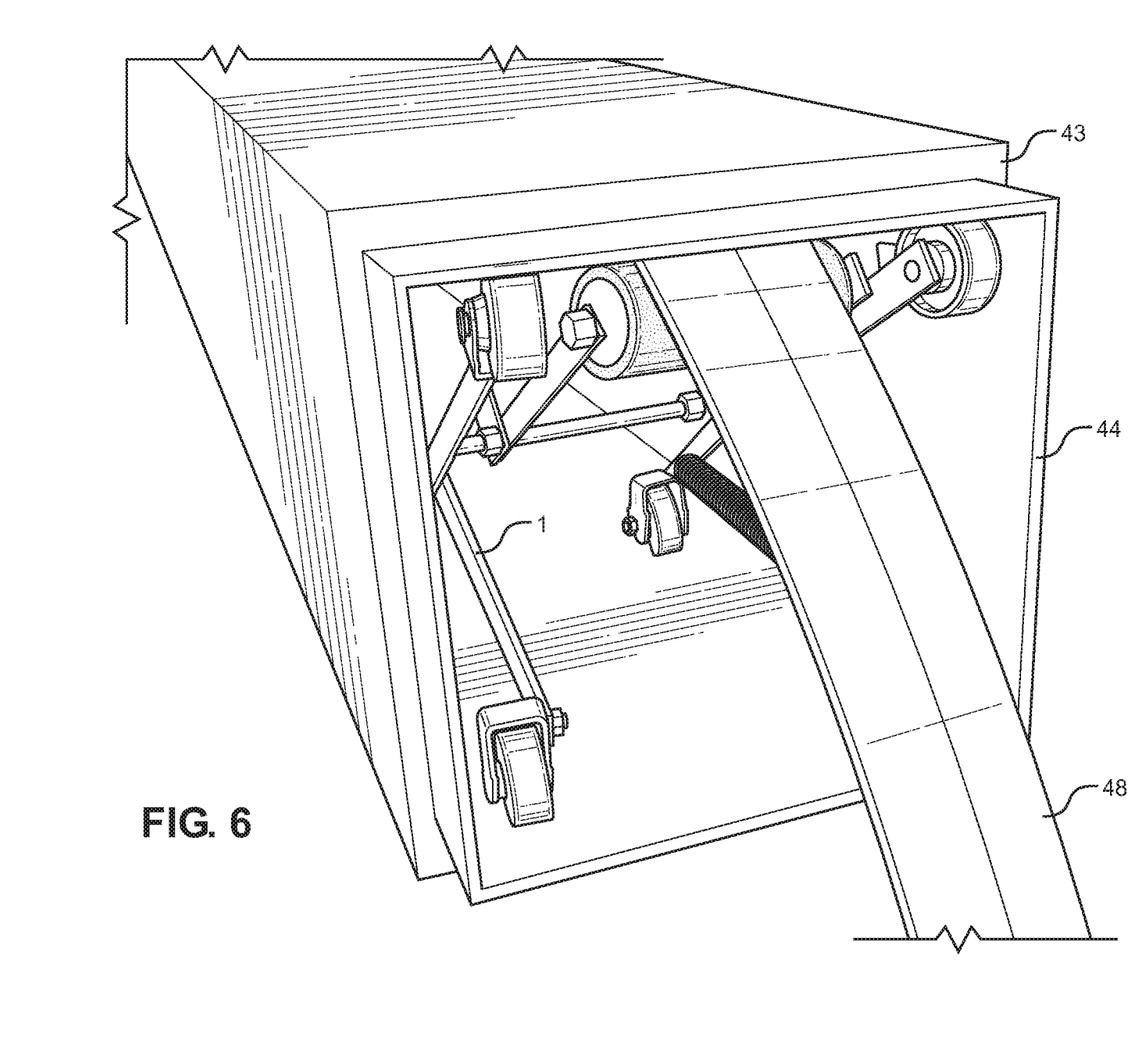
FIG. 6 depicts a perspective view of an exemplary use of the installation device in a method for installing a plurality of UV LEDs into an air duct.

Referring now to FIG. 6, there is depicted a perspective view of an exemplary use of the installation device in a method for installing a plurality of UV LEDs into an air duct. Generally, a method for installing a plurality of ultraviolet light-emitting diodes (UV LEDs) in an air duct comprises exerting an upward force to press the plurality of UV LEDs against an upper surface of an interior of the air duct, and guiding the upward force along the interior of the air duct. In the shown embodiment, the plurality of UV LEDs includes a UV LED strip 48, and the air duct includes a metallic air duct 43 having a metallic air duct opening 44. In the shown embodiment, upon applying the upward force, the plurality of UV LEDs are secured to the upper surface of the interior of the air duct by a ferromagnet. In some embodiments, upon applying the upward force, the plurality of UV LEDs are secured to the upper surface of the interior of the air duct by an adhesive, such as an expanding adhesive, as described elsewhere herein. After installing the plurality of UV LEDs into the air duct, an electrical energy is provided to the plurality of UV LEDs to cause an ultraviolet light to be emitted from the plurality of UV LEDs. Providing the electrical energy to the plurality of UV LEDs configures the air duct sterilization system to sterilize the air duct.

Figure 7:
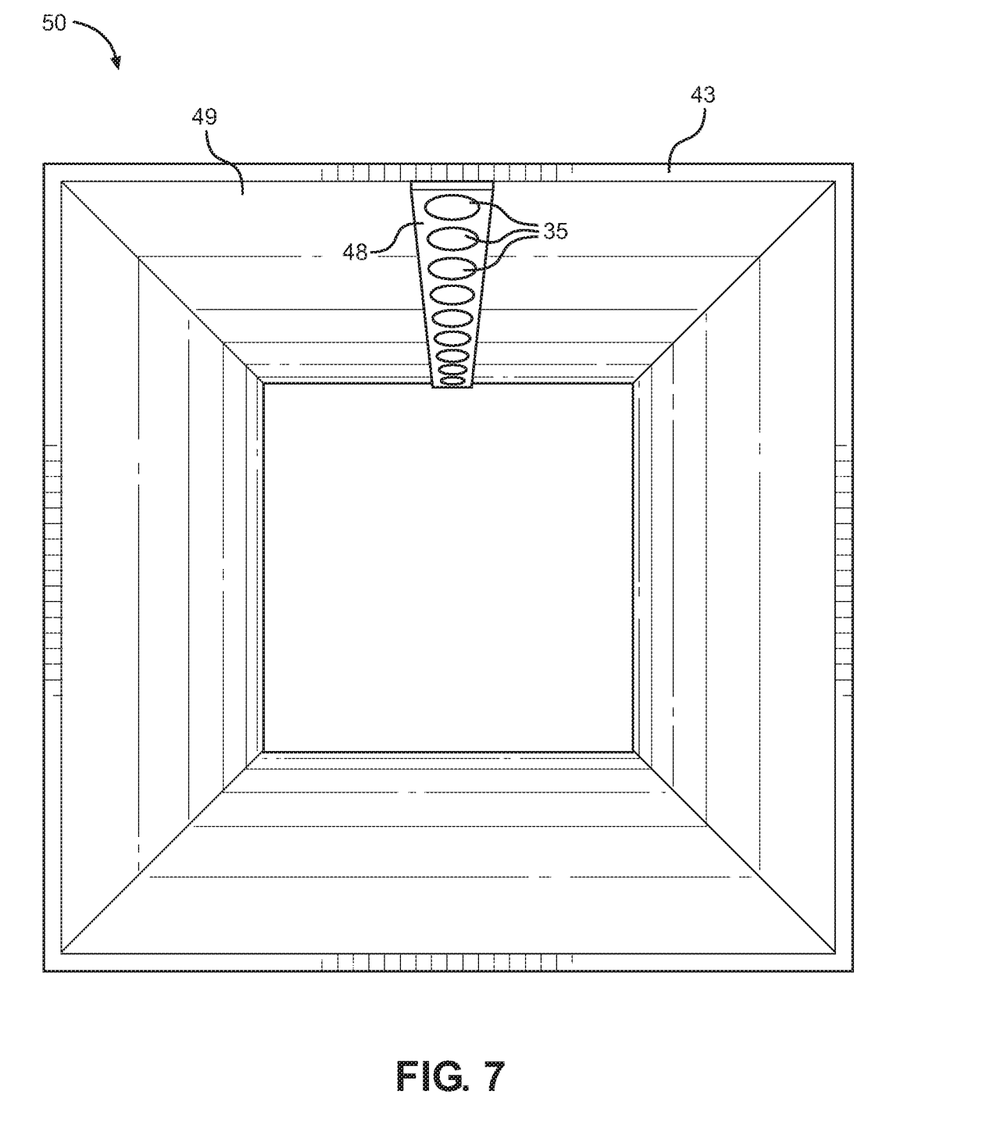
FIG. 7 depicts a perspective view of the exemplary air duct sterilization system, produced by the method utilizing the installation device.

Referring now to FIG. 7, there is depicted a perspective view of the exemplary air duct sterilization system, produced by the method utilizing the installation device. An air duct sterilization system 50 includes an air duct, and a plurality of UV LEDs 35 secured to an upper surface of an interior of the air duct. In the shown embodiment, the air duct includes a metallic air duct 43, and a UV LED strip 48 is attached to an upper surface 49 of the interior of the metallic air duct 43, as described elsewhere herein. As such, the UV LED strip 48 is attached to the upper surface 49 by a ferromagnet, as described elsewhere herein. In some embodiments, the UV LED strip 48 is attached to an upper surface of a non-magnetic air duct by an adhesive, as described elsewhere herein. After installing the plurality of UV LEDs into the air duct, an electrical energy is provided to the plurality of UV LEDs to cause an ultraviolet light to be emitted from the plurality of UV LEDs. Providing the electrical energy to the plurality of UV LEDs configures the air duct sterilization system to sterilize the air duct.

In some embodiments, the plurality of UV LEDs is installed onto a length of the air duct that is horizontal within a building. In this case, the plurality of UV LEDs are installed such that any dust or debris that may accumulate in the air duct will not interfere with an operation of the UV LEDs. To achieve this, the UV LEDs are installed onto the upper surface of the interior of the air duct. After installation, the electrical energy is supplied to the plurality of UV LEDs from the power supply.

The foregoing descriptions of specific embodiments of the present invention have been presented for purposes of illustration and description. They are not intended to be exhaustive or limit the present invention to the precise forms disclosed, and modifications and variations are possible in view of the above teaching. The exemplary embodiment was chosen and described to best explain the principles of the present invention and its practical application, to thereby enable others skilled in the art to best utilize the present invention and its embodiments with modifications as suited to the use contemplated.

It is therefore submitted that the present invention has been shown and described in the most practical and exemplary embodiments. It should be recognized that departures may be made which fall within the scope of the invention. With respect to the description provided herein, it is submitted that the optimal features of the invention include variations in size, materials, shape, form, function and manner of operation, assembly, and use. All structures, functions, and relationships equivalent or essentially equivalent to those disclosed are intended to be encompassed by the present invention.

I claim:

1. A device for installing a plurality of ultraviolet light-emitting diodes (UV LEDs) in an air duct, comprising:
    a central axle;
    a left wheel assembly disposed on a left end of the central axle, wherein the left wheel assembly includes a plurality of left guide wheels disposed thereon configured to guide the device through the air duct during installation of the plurality of UV LEDs;
    a right wheel assembly disposed on a right end of the central axle, wherein the right wheel assembly includes a plurality of right guide wheels disposed thereon configured to guide the device through the air duct during installation of the plurality of UV LEDs;
    an applicator assembly disposed on an intermediate portion of the central axle between the left end and the right end thereof, wherein the applicator assembly includes a plurality of applicator rolls configured to exert an upward force to press the plurality of UV LEDs against an upper surface of an interior of the air duct during installation of the plurality of UV LEDs.

2. The device of claim 1, wherein the left wheel assembly includes a first guide leg pivotally disposed on the left end of the central axle, and a second guide leg pivotally disposed on the left end of the central axle;
    wherein the right wheel assembly includes a third guide leg pivotally disposed on the right end of the central axle, and a fourth guide leg pivotally disposed on the right end of the central axle.

3. The device of claim 2, wherein the first guide leg and the second guide leg are connected in a scissor configuration and are biased by a biasing mechanism configured to apply an upward stabilizing force to the upper surface of the interior of the air duct during installation of the plurality of UV LEDs;
    wherein the third guide leg and the fourth guide leg are connected in a scissor configuration and are biased by a biasing mechanism configured to apply the upward stabilizing force to the upper surface of the interior of the air duct during installation of the plurality of UV LEDs.

4. The device of claim 3, wherein the biasing mechanism of the first guide leg and the second guide leg includes a left upper spring attached on a forward end thereof to an upper portion of the first guide leg, and attached on a rearward end thereof to an upper portion of the second guide leg;
    wherein the biasing mechanism of the third guide leg and the fourth guide leg includes a right upper spring attached on a forward end thereof to an upper portion of the third guide leg, and attached on a rearward end thereof to an upper portion of the fourth guide leg.

5. The device of claim 4, wherein the biasing mechanism of the first guide leg and the second guide leg includes a left lower spring attached on a forward end thereof to a lower portion of the first guide leg, and attached on a rearward end thereof to a lower portion of the second guide leg;
    wherein the biasing mechanism of the third guide leg and the fourth guide leg includes a right lower spring attached on a forward end thereof to a lower portion of the third guide leg, and attached on a rearward end thereof to a lower portion of the fourth guide leg.

6. The device of claim 1, wherein the plurality of applicator rolls includes a forward applicator roll and a rearward applicator roll;
    wherein the forward applicator roll is rotatably attached to a forward applicator axle;
    wherein the rearward applicator roll is rotatably attached to a rearward applicator axle;
    wherein a left forward applicator arm is rotatably attached to a left end of the forward applicator axle and pivotally attached to the intermediate portion of the central axle;
    wherein a right forward applicator arm is rotatably attached to a right end of the forward applicator axle and pivotally attached to the intermediate portion of the central axle;
    wherein a left rearward applicator arm is rotatably attached to a left end of the rearward applicator axle and pivotally attached to the intermediate portion of the central axle;
    wherein a right rearward applicator arm is rotatably attached to a right end of the rearward applicator axle and pivotally attached to the intermediate portion of the central axle.

7. The device of claim 6, wherein the left forward applicator arm and the left rearward applicator arm are connected in a scissor configuration and are biased by a biasing mechanism configured to apply the upward force to the upper surface of the interior of the air duct during installation of the plurality of UV LEDs;

wherein the right forward applicator arm and the right rearward applicator arm are connected in a scissor configuration and are biased by a biasing mechanism configured to apply the upward force to the upper surface of the interior of the air duct during installation of the plurality of UV LEDs.

8. The device of claim 7, wherein the biasing mechanism of the left forward applicator arm and the left rearward applicator arm includes a left applicator spring attached on a forward end thereof to an upper portion of the left forward applicator arm, and attached on a rearward end thereof to an upper portion of the left rearward applicator arm;

wherein the biasing mechanism of the right forward applicator arm and the right rearward applicator arm includes a right applicator spring attached on a forward end thereof to an upper portion of the right forward applicator arm, and attached on a rearward end thereof to an upper portion of the right rearward applicator arm.

9. The device of claim 2, wherein the plurality of left guide wheels includes a left lower rearward wheel disposed on a lower end of the first guide leg, and a left lower forward wheel disposed on a lower end of the second guide leg;

wherein the plurality of right guide wheels includes a right lower rearward wheel disposed on a lower end of the third guide leg, and a right lower forward wheel disposed on a lower end of the fourth guide leg;

wherein the left lower forward wheel, the left lower rearward wheel, the right lower forward wheel, and the right lower rearward wheel are configured to contact a lower surface of the interior of the air duct during installation of the plurality of UV LEDs.

10. The device of claim 9, wherein the plurality of left guide wheels includes a left upper forward wheel disposed on an upper end of the first guide leg, and a left upper rearward wheel disposed on an upper end of the second guide leg;

wherein the plurality of right guide wheels includes a right upper forward wheel disposed on an upper end of the third guide leg, and a right upper rearward wheel disposed on an upper end of the fourth guide leg;

wherein the left upper forward wheel, the left upper rearward wheel, the right upper forward wheel, and the right upper rearward wheel are configured to contact the upper surface of the interior of the air duct during installation of the plurality of UV LEDs.

11. A method for installing a plurality of ultraviolet light-emitting diodes (UV LEDs) in an air duct, comprising:

exerting an upward force to press the plurality of UV LEDs against an upper surface of an interior of the air duct;

guiding the upward force along the interior of the air duct.

12. The method of claim 11, whereupon applying the upward force, the plurality of UV LEDs are secured to the upper surface of the interior of the air duct by a ferromagnet.

13. The method of claim 12, further comprising providing an electrical energy to the plurality of UV LEDs, whereupon providing the electrical energy, an ultraviolet light is emitted from the plurality of UV LEDs.

14. The method of claim 11, whereupon applying the upward force, the plurality of UV LEDs are secured to the upper surface of the interior of the air duct by an adhesive.

15. The method of claim 14, further comprising providing an electrical energy to the plurality of UV LEDs, whereupon providing the electrical energy, an ultraviolet light is emitted from the plurality of UV LEDs.

* * * * *